United States Patent
Cernasov et al.

(10) Patent No.: US 8,236,331 B2
(45) Date of Patent: Aug. 7, 2012

(54) COSMETIC COOLING COMPOSITION

(75) Inventors: Domnica Cernasov, Ringwood, NJ (US); Bhal Moghe, White House Station, NJ (US); Amit Patel, Pine Prook, NJ (US); Thomas Schamper, Cranbury, NJ (US); Donna Hui-Ing Hwang, Leonia, NJ (US); Anthony Esposito, Roselle, NJ (US)

(73) Assignee: Coty Deutschland GmbH, Mainz (DE)

( * ) Notice: Subject to any disclaimer, the term of this patent is extended or adjusted under 35 U.S.C. 154(b) by 979 days.

(21) Appl. No.: 11/664,509

(22) PCT Filed: Sep. 13, 2005

(86) PCT No.: PCT/EP2005/009992
§ 371 (c)(1),
(2), (4) Date: Jul. 11, 2008

(87) PCT Pub. No.: WO2006/037448
PCT Pub. Date: Apr. 13, 2006

(65) Prior Publication Data
US 2008/0267889 A1    Oct. 30, 2008

(30) Foreign Application Priority Data
Oct. 4, 2004  (DE) .................. 10 2004 048 987

(51) Int. Cl.
*A61K 8/02* (2006.01)
*A61K 31/19* (2006.01)
*A61K 31/195* (2006.01)
*A61K 31/21* (2006.01)

(52) U.S. Cl. ......... 424/401; 514/506; 514/563; 514/785

(58) Field of Classification Search .................. 424/401; 514/506, 563, 785
See application file for complete search history.

(56) References Cited

U.S. PATENT DOCUMENTS

| | | | |
|---|---|---|---|
| 5,703,123 A * | 12/1997 | Pelzer et al. | 514/512 |
| 5,725,865 A | 3/1998 | Mane | |
| 6,267,974 B1 | 7/2001 | Suares | |
| 6,897,195 B2 * | 5/2005 | Su et al. | 512/1 |

FOREIGN PATENT DOCUMENTS

| | | | |
|---|---|---|---|
| EP | 0988852 A2 | 3/2000 | |
| GB | 2233873 A | 1/1991 | |
| JP | 02191540 | 7/1990 | |
| JP | 07196707 | 8/1995 | |
| JP | 2001226252 | 8/2001 | |
| JP | 2002080335 | 3/2002 | |
| JP | 2002536069 | 10/2002 | |
| WO | 9400109 A1 | 1/1994 | |
| WO | 0042983 A1 | 7/2000 | |
| WO | WO 00/45815 | * | 8/2000 |
| WO | 03007909 A2 | 1/2003 | |

OTHER PUBLICATIONS

Erman, M. B. "Cooling Agents and Skin Care Applications," Cosmetics & Toiletries, May 2005, 120(5), pp. 105-118.*

* cited by examiner

*Primary Examiner* — James H. Alstrum-Acevedo
(74) *Attorney, Agent, or Firm* — Novak Druce + Quigg LLP

(57) ABSTRACT

The invention relates to a cosmetic composition having a cooling effect, particularly a clear gel or a spray. The composition has a long-lasting cooling effect of about 8 hours and comprises a cooling complex consisting of 0.05-0.15% Menthyl Lactate, 0.1-0.2% Menthyl PCA and 0.05-0.2% Ethyl Menthane Carboxamide.

12 Claims, No Drawings

COSMETIC COOLING COMPOSITION

The present invention relates to a cosmetic composition having a cooling effect, particularly a clear gel.

A cosmetic cooling composition is known from EP 988852, which consists of menthol, isopulegol, 3-(menthoxy)propane-1,2-diol, p-menthane-3,8-diol and vanillyl butyl ether. The composition is said to have a good cooling effect and, in addition, a long-lasting effect. A comparative test indicates a long-lasting effect of up to 90 minutes. WO 03/007909 describes the cooling effect of methyl palmitate as "long-lasting" without specifying a period of time. U.S. Pat. No. 6,267,974 discloses a mixture of menthyl lactate, isopulegol and menthoxypropanediol as a long-lasting cooling mixture, describing cooling times of 30 minutes in the example.

The object of the invention is to provide a cooling composition, preferably a cooling gel or a spray, which has a long-lasting cooling effect of at least 120 minutes.

It is a further object of the invention to provide a cooling composition, preferably a clear gel or a spray, whose cooling effect last for up to 8 hours.

According to the invention, the composition comprises a cooling complex consisting of 0.05-0.15% Menthyl Lactate, 0.1-0.2% Menthyl PCA and 0.05-0.2% Ethyl Menthane Carboxamide, and a remainder up to 100% of further cosmetic auxiliaries, active agents or mixtures thereof, wherein all percentages are in % by weight relative to the composition's total weight.

Menthyl PCA is the INCI name of menthol which has been esterified with pyrrolidone carboxylic acid (PCA).

In a first preferred embodiment of the invention the composition is a clear gel. The gel comprises the cooling complex consisting of 0.05-0.15% Menthyl Lactate, 0.1-0.2% Menthyl PCA and 0.05-0.2% Ethyl Menthane Carboxamide, and additionally at least 7-25% of a silicone oil or silicone oil mixture, 10-35% of an alcohol or alcohol mixture and 5-20% water.

A silicone oil mixture according to the invention advantageously consists of 5-15% of a volatile silicone oil such as Cyclopentasiloxane, 0.1-1% of a polymethyl siloxane such as Dimethicone and 2-7% of a silicone oil which has been derivatised with polyethylene/polypropylene glycol such as PEG/PPG-18/18 Dimethicone.

The alcohol mixture preferably consists of a monovalent and a polyvalent alcohol. Preferably, an alcohol mixture is used which contains 5-20% of the monovalent alcohol and 5-15% of the polyvalent alcohol. A preferred monovalent alcohol is ethanol and a preferred polyvalent alcohol is glycerine, propylene glycol or butylene glycol.

Further cosmetic active agents which may be added to the gel include e.g. organic sunscreens, scavengers, moisturizers, vitamins, enzymes, plant-based active agents, antioxidants, anti-inflammatory natural active agents and asymmetric lamellar aggregates loaded with oxygen according to WO 94/00109, provided they do not impair the gel's clarity.

Another preferred cosmetic active agent contained in the cosmetic cooling composition, preferably in the gel, is an antiperspirant, such as aluminium chlorohydroxide, aluminium zirconium chlorohydroxide (Aluminium Zirconium Tetrachlorohydrex GLY), among others.

The gel according to the invention further contains cosmetic auxiliaries and carriers as they are commonly used in such preparations, e.g. preservatives, colourants, thickeners, fragrances, polar and non-polar oils, polymers, copolymers, emulsifiers, stabilizers, provided they do not impair the gel's clarity.

Another embodiment relates to the use of a cooling complex consisting of 0.05 to 0.15% Menthyl Lactate, 0.1 to 0.2% Menthyl PCA and 0.05 to 0.2% Ethyl Menthane Carboxamide for applying on a human skin as a cosmetic clear gel or spray together with a remainder up to 100% of further cosmetic auxiliaries, active agents or mixtures thereof, wherein all percentages are in % by weight relative to the gel's or spray's total weight.

Examples of thickeners are e.g. silicone resins or gums.

Examples of oils are e.g. esters and hydrocarbons.

Suitable esters are Dipentaerythrityl Hexacaprylate/Hexacaprate/Tridecyl Trimellitate/Tridecyl Stearate/Neopentyl Glycol Dicaprylate Dicaprate, Propylene Glycol Dioctanoate 5, Propylene Glycol Dicaprylate 2,30 Dicaprate, Tridecyl Stearate/neopentyl glycol dicaprylate dicaprate/tridecyl trimellitate, Neopentyl Glycol Dioctanoate, Isopropyl Myristate, Diisopropyl Dimer Dilinoleate, Trimethylpropane Triisostearate.

Examples of emulsifiers are e.g. ethoxylated and/or propoxylated fatty alcohols and fatty acids, e.g. of $C_8$-$C_{22}$ fatty alcohols and of $C_{12}$-$C_{22}$ fatty acids.

In a further preferred embodiment of the invention the composition is a cooling spray, preferred a deodorant spray and comprises the above mentioned cooling complex and 30-75% of a monovalent alcohol, 0-2% of a multivalent alcohol and 20-65% of propellants.

Said propellants are e.g. one or more hydrofluorocarbons in the range of 20-35% or one or more $C_3$-$C_5$ alkanes in the range of 45-65%.

The deodorant spray comprises preferably up to 0.01% by weight 4-(butoxymethyl)-2-methoxyphenol as a further cooling agent.

Further embodiments of the present invention can be prepared on basis of water, e.g. 80-95% (all are % by weight), as a gel and with addition of crosspolymers, or on basis of propylene glycol (PG), e.g. 60-80% PG, or as a water-based body wash with 30-45% water and 20-60% wash active substances such as laureth sulfates, betains etc., or as decorative cosmetics e.g. eye shadow with 85-95% water, 0.2-1.5% glycerine, 1-5% PVP (polyvinyl pyrrolidone) and 1-5% polyacrylates, or as a lip gloss with 30-50% water, 0.5-12% wax and polyethylene, respectively, and other usual auxiliaries such as e.g. Versagel ME1600, all of them together with the cooling complex of the invention.

Surprisingly, it has been found that a complex of the aforementioned menthane derivatives, each of which has a certain cooling effect, even if used alone, has a particularly long-lasting cooling effect of up to 8 hours if it is combined with the other substantial components of the complex in a cosmetic composition. Particularly preferred are clear gels, and especially those clear gels containing a total of menthane derivatives not exceeding 0.5% by weight, especially those containing not more than 0.3% by weight, wherein Menthyl PCA does not make up more than 0.25% by weight, preferred 0.15% by weight. It is particularly preferred that Menthyl Lactate be contained in an amount of $\leq 0.1\%$ by weight, all percentages being relative to the gel's total weight.

The gel according to the invention has a cooling effect lasting for at least 2 hours, particularly for 3-6 hours and particularly preferred for up to 8 hours. This has been confirmed by means of tests.

The invention will now be explained in more detail by means of examples. All percentages are in % by weight unless indicated otherwise.

EXAMPLE 1

Clear Anti-Sweat Body Gel

| Phase A | |
|---|---|
| Cyclopentasiloxane | 9.0 |
| Dimethicone | 0.45 |
| PEG/PPG-18/18 Dimethicone | 2.9 |
| Triethyl Citrate | 0.12 |
| Farnesol | 0.05 |
| Phase B | |
| Aluminum Zirconium Tetrachlorohydrex GLY (35% solution) | 54.0 |
| Water | q.s. ad 100 |
| Dipropylene Glycol | 6.9 |
| Ethanol | 15.0 |
| Phase C | |
| Menthyl Lactate | 0.075 |
| Menthyl PCA | 0.12 |
| Ethyl Menthane Carboxamide | 0.08 |
| Dipropylene Glycol | 0.225 |
| Phase D | |
| Fragrance | 0.75 |

Phase A and phase B are prepared separately while mixing. Phase B is added slowly to phase A and the product is mixed for 5 to 10 minutes. Phase C is prepared while moderately mixing at 50-55° C. until all ingredients are dissolved in the presence of a part of dipropylene glycol. Phase C is added to the mixture of phases A and B and after that phase D is introduced also while mixing. The batch is homogenized to a viscosity of 100000-150000 mPa·s (cP), measured by Brookfield, Spindle TC/TD/TE at 25° C. and in the range of 50-75% of the spindle rpm's.

EXAMPLE 2

Cooling Deodorant Spray I

| Propylene Glycol | 1.4 |
|---|---|
| Ethanol | q.s. ad 100 |
| Menthyl Lactate | 0.09 |
| Menthyl PCA | 0.11 |
| Ethyl Menthane Carboxamide | 0.9 |
| Vanillyl butyl ether | 0.005 |
| Triethyl Citrate | 0.2 |
| Farnesol | 0.1 |
| Fragrance | 1.4 |
| Hydrofluorocarbon 152A | 28 |

In the solvent are introduced step-by-step Propylene glycol, Triethyl Citrate, Farnesol, the cooling ingredients and fragrance. The mixture is stirred for 10-15 minutes, filled in spray containers and the propellant added.

EXAMPLE 3

Cooling Deodorant Spray II

| Propylene Glycol | 1.3 |
|---|---|
| Ethanol | q.s. ad 100 |
| Menthyl Lactate | 0.05 |
| Menthyl PCA | 0.14 |
| Ethyl Menthane Carboxamide | 0.11 |
| Vanillyl butyl ether | 0.004 |
| Triethyl Citrate | 0.2 |
| Farnesol | 0.1 |
| Fragrance | 1.2 |
| A-46 (butane, isobutane, propane) | 60 |

EXAMPLE 4

Cooling Deodorant Gel

| Phase A | |
|---|---|
| Water | 19 |
| Propylene Glycol | q.s. ad 100 |
| Phase B | |
| Menthyl Lactate | 0.075 |
| Menthyl PCA | 0.12 |
| Ethyl Menthane Carboxamide | 0.08 |
| Propylene Glycol | 0.223 |
| Vanillyl butyl ether | 0.003 |
| Phase C | |
| Triclosan | 0.2 |
| Fragrance | 2.0 |
| Phase D | |
| Color solutions | 0-2 |

Phase A is heated by 75° C. while stirring. The ingredients of phase B are mixed and added as phase B to phase A. At about 65° C. phase C is added and after that phase D.

EXAMPLE 5

Cooling Body Gel

| Basics | |
|---|---|
| Water | q.s. ad 100 |
| Ammonium Acryloyldimethyltaurate/Beheneth-25 Methacrylate Crosspolymer | 0.5 |
| Panthenol | 1.0 |
| Ethanol | 0.4 |
| Cooling part | |
| Menthyl Lactate | 0.075 |
| Menthyl PCA | 0.25 |
| Ethyl Menthane Carboxamide | 0.2 |
| Allyl Methacrylates Crosspolymer | 0.05 |
| Vanillyl butyl ether | 0.006 |

EXAMPLE 6

Cooling Body Cream

| Other ingredients | |
|---|---|
| Basics | |
| Water | q.s. ad 100 |
| Dimethicone | 9.0 |
| Dimethicone Copolyol Crosspolymer | 3.0 |
| Glycerine | 10 |
| Cooling part | |
| Menthyl Lactate | 0.075 |
| Menthyl PCA | 0.25 |
| Ethyl Menthane Carboxamide | 0.2 |
| Allyl Methacrylates Crosspolymer | 0.05 |
| Vanillyl butyl ether | 0.006 |
| Other ingredients | |
| Fragrance | 1.0 |
| Preservatives | 1.0 |

EXAMPLE 7

Cooling Body Wash

| Basics | |
|---|---|
| Water | q.s. ad 100 |
| Sodium Laureth Sulfate | 30 |
| Cocamidopropyl Betaine | 20 |
| PEG-30 Glyceryl Stearate | 3 |
| Citric acid | 0.1 |
| Glycerine | 10 |
| Cooling part | |
| Menthyl Lactate | 0.075 |
| Menthyl PCA | 0.25 |
| Ethyl Menthane Carboxamide | 0.2 |
| Allyl Methacrylates Crosspolymer | 0.05 |
| Vanillyl butyl ether | 0.006 |
| Other components | |
| Fragrance | 1.0 |
| Preservatives | 1.0 |

EXAMPLE 8

Cooling Eye Shadow

| Basics | |
|---|---|
| Water | q.s. ad 100 |
| Butylene Glycol | 0.2 |
| Triethanolamine | 0.2 |
| Sorbitan Sesquioleate | 0.2 |
| PVP | 2 |
| Citric acid | 0.1 |
| Glycerine | 0.8 |
| Cooling part | |
| Menthyl Lactate | 0.075 |
| Menthyl PCA | 0.25 |
| Ethyl Menthane Carboxamide | 0.2 |
| Allyl Methacrylates Crosspolymer | 0.05 |
| Vanillyl butyl ether | 0.006 |
| Other components | |
| Fragrance | 1.0 |
| Preservatives | 1.0 |

EXAMPLE 9

Cooling Lip Gloss

| Basics | |
|---|---|
| Water | q.s. ad 100 |
| Proplipid 141 | 3 |
| Synthetic wax | 4 |
| Polyethylene | 2.8 |
| Cetyl PEG/PPG-10/1 Dimethicone | 2 |
| Stearyl Dimethicone | 10 |
| Polyglyceryl-3 Diisostearate | 2 |
| Phenyl Trimethicone | 2 |
| Hydrogenated Polyisobutene | 10 |
| Bis PEG-18 Methylether Dimethylsilane | 3 |
| Castor Oil and $TiO_2$ | 1.5 |
| Versagel ME1600 | 7 |
| Cooling part | |
| Menthyl Lactate | 0.1 |
| Menthyl PCA | 0.2 |
| Ethyl Menthane Carboxamide | 0.1 |
| Vanillyl butyl ether | 0.03 |
| Other components | |
| Fragrance | 1.0 |
| Preservatives | 0.5 |
| Colorant | 8 |

EXAMPLE 10

Cooling Activity Test

A group of panelists were participants in a study of the cooling effect of the compositions of the invention.

A cosmetic gel of example 1 (TEST) was applied to one underarm of all panelists (active side) and a gel of example 1 without the ingredients of the cooling complex (CONTROL) was applied to the other underarm of the panelists (passive side).

Following the first application the panelists had to perform several tasks:
(1) sit in a sauna for 15 mins
(2) take a shower
(3) enter a whirlpool
(4) enter a pool
(5) take another shower.

Then the panelists had to apply the products for a second time (amount about ½ inch through a package applicator) and were asked to refrain from taking another shower until the following morning, 24 hours after the first application.

The comments the panelists made about cooling sensations or other sensations were recorded at several points in time:
(1) immediately after the first application
(2) post-sauna
(3) post-shower/whirlpool/pool/second shower
(4) immediately after the second application
(5) 8 hours after the first application
(6) 24 hours after the first application Results: All panelists perceived a greater cooling sensation on the active side than of the passive side which sensation increased in intensity during activities such as showering, sitting in the sauna, sitting in the whirlpool or swimming. The significant cooling sensation felt by all panelists lasted for approximately 8 hours. None of the panelists perceived a cooling sensation 24 hours after application.

The test shows the superiority of the cosmetic composition of the invention over known cooling compositions which had effects of 30-90 minutes only.

The invention claimed is:

1. A cosmetic composition having a cooling effect which comprises a cooling complex consisting of
   0.05 to 0.1% Menthyl Lactate,
   0.1-0.2% Menthyl PCA and
   0.05-0.2% Ethyl Menthane Carboxamide and
   a remainder up to 100% of cosmetic auxiliaries, active agents or mixtures thereof,
wherein all percentages are in % by weight relative to the composition's total weight.

2. A cosmetic cooling composition according to claim 1, wherein the composition is a clear gel and comprises the cooling complex consisting of
   0.05 to 0.1% Menthyl Lactate,
   0.1-0.2% Menthyl PCA and
   0.05-0.2% Ethyl Menthane Carboxamide and
   7-25% of a silicone oil or silicone oil mixture,
   10-35% of an alcohol or alcohol mixture,
   5-20% water and
   a remainder up to 100% of further cosmetic auxiliaries, active agents or mixtures thereof,
wherein all percentages are in % by weight relative to the composition's total weight.

3. A cosmetic cooling composition according to claim 2, wherein said silicone oil mixture comprises
   5-15% Cyclopentasiloxane,
   0.1-1% Dimethicone and
   2-7% PEG/PPG-18/18 Dimethicone.

4. A cosmetic cooling composition according to claim 2, wherein said alcohol mixture consists of a monovalent and a polyvalent alcohol.

5. A cosmetic cooling composition according to claim 4, wherein said monovalent alcohol is in the range of 5-20% and said polyvalent alcohol is in the range of 5-15%.

6. A cosmetic cooling composition according to claim 2, wherein an antiperspirant is contained as a further cosmetic active agent.

7. A cosmetic cooling composition according to claim 1, wherein the composition is a cooling spray and comprises the cooling complex and 30-75% by weight of a monovalent alcohol, 0-2% by weight of a multivalent alcohol and 20-65% by weight of propellants, relative to the composition's total weight.

8. A cosmetic cooling composition according to claim 7, wherein said propellants are one or more hydrofluorocarbons in the range of 20-35%.

9. A cosmetic cooling composition according to claim 7, wherein said propellants are one or more $C_3$-$C_5$ alkanes in the range of 45-65%.

10. A cosmetic cooling composition according to claim 7, wherein the spray comprises up to 0.01% 4-(butoxymethyl)-2-methoxyphenol.

11. A method of treating human skin in need of a cooling treatment, the method comprising the step of topically applying the cosmetic cooling composition according to claim 2 in the form of a gel to the skin to be cooled.

12. A method of treating human skin in need of a cooling treatment, the method comprising the step of topically applying the cosmetic cooling composition according to claim 2 as a spray to the skin to be cooled.

* * * * *

UNITED STATES PATENT AND TRADEMARK OFFICE
CERTIFICATE OF CORRECTION

| | |
|---|---|
| PATENT NO. | : 8,236,331 B2 |
| APPLICATION NO. | : 11/664509 |
| DATED | : August 7, 2012 |
| INVENTOR(S) | : Domnica Cernasov et al. |

It is certified that error appears in the above-identified patent and that said Letters Patent is hereby corrected as shown below:

Page 5, Col. 7, Line 34 should read 0.05 to < 0.1% Menthyl Lactate,

Signed and Sealed this
First Day of January, 2013

David J. Kappos
*Director of the United States Patent and Trademark Office*